(12) United States Patent
Sugihara et al.

(10) Patent No.: US 6,297,025 B1
(45) Date of Patent: *Oct. 2, 2001

(54) MEASUREMENT OF COMPLETE ELECTRICAL WAVEFORMS OF TISSUE OR CELLS

(75) Inventors: Hirokazu Sugihara, Osaka; Akihito Kamei, Nara; Yasushi Kobayashi, Osaka; Makoto Taketani, Kyoto; Tadayasu Mitsumata, Osaka, all of (JP)

(73) Assignee: Matsushita Electric Industrial Co., LTD, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/662,629

(22) Filed: Jun. 13, 1996

Related U.S. Application Data

(63) Continuation-in-part of application No. 08/464,116, filed on Jun. 5, 1995, now Pat. No. 5,563,067.

(30) Foreign Application Priority Data

Jun. 13, 1994 (JP) .................................................. 6-130176

(51) Int. Cl.[7] ............................. C12Q 1/02; C12M 3/04; G01N 27/00; C12N 13/00
(52) U.S. Cl. .................................. 435/29; 435/5; 435/6; 435/283.1; 435/285.2; 435/173; 435/287.2; 435/288.7; 364/496; 324/437; 324/444; 324/445; 324/447; 422/82.01
(58) Field of Search ............................. 435/287.2, 288.7, 435/7.1–7.9, 5, 6, 291, 296, 297, 298, 301, 817, 173.1; 364/496, 482, 483; 422/82.01; 324/439, 444, 445, 446, 447, 450, 691, 692

(56) References Cited

U.S. PATENT DOCUMENTS

| 4,072,578 | 2/1978 | Cody et al. | |
|---|---|---|---|
| 4,856,073 | * 8/1989 | Farber et al. | 382/6 |
| 5,187,096 | * 2/1993 | Giaver et al. | 435/291 |
| 5,432,086 | * 7/1995 | Franzel et al. | 435/291 |
| 5,563,067 | * 10/1996 | Sugihara et al. | 435/287.1 |
| 5,759,846 | * 6/1998 | Stoppini et al. | 435/284.1 |

FOREIGN PATENT DOCUMENTS

| 0 585 933 A2 | 3/1994 | (EP) . |
|---|---|---|
| 55-84148 | 6/1980 | (JP) . |
| 63-84476 | 4/1988 | (JP) . |
| 3-265814 | 11/1991 | (JP) . |
| 4-204244 | 7/1992 | (JP) . |

OTHER PUBLICATIONS

Ambros–Ingerson et al, "Waveform analysis suggests that LTP alters the kinetics of synaptic receptor channels", Brain Research 620:237–244, 1993.*
Patent Abstracts of Japan, vol. 016, No. 75 (P–1316), Feb. 24, 1992 & JP–03–265814 A (Olympus Optical Co. Ltd.), Nov. 26, 1991 abstract considered.
Journal of Neuroscience Methods, vol. 5, 1982, Amsterdam, NL, pp: 13–22, XP002037335 G.W. Gross et al., "Recording of spontaneous activity with photoetched microelectrode surfaces from mouse spinal neurons in culture".
Biosensors & Bioelectronics 9 (1994), 2nd CEC Workshop on Bioelectronics: Interfacing Biology with Elecctronics, Preface.
Biosensors & Bioelectronics 9 (1994) pp: 737–741, A thin film microelectrode array for monitoring extracellular neuronal acitivity in vitro, W. Nisch, J. Böck, U. Egert, H. Hämmerle & A. Mohr.

* cited by examiner

Primary Examiner—Jeffrey Fredman
(74) Attorney, Agent, or Firm—Morrison & Foerster LLP

(57) ABSTRACT

A method of observing a physical and chemical property of a tissue or cell by using an apparatus which comprises at least a cell culturing means, an environment conditioning means, an observing means and a comparing means, comprising the steps of (A) culturing the tissue or cell by the cell culturing means, (B) maintaining a first physical and chemical environment around the tissue or cell by the cell culturing means, (C) observing a first physical and chemical property of the tissue or cell in the first physical and chemical environment by the observing means, (D) changing the first physical and chemical environment to a second physical and chemical environment by the environment conditioning means, (E) observing a second physical and chemical property of the tissue or cell in the second physical and chemical environment by the observing means, and (F) comparing the first physical and chemical property of the tissue or cell with the second physical and chemical property of the tissue or cell by the comparing means.

15 Claims, 8 Drawing Sheets

MEASUREMENT OF COMPLETE ELECTRICAL WAVEFORMS OF TISSUE OR CELLS

The application is a continuation-in-part of U.S. patent application Ser. No. 08/464,116 filed Jun. 5, 1995 which is incorporated herein by reference, now U.S. Pat. No. 5,563,067.

FIELD OF THE INVENTION

The invention relates to a method for observing physical and chemical properties of biological tissues and cells, and an apparatus for use in such method. The method and apparatus are mainly used in the fields of environmental science, medical science, pharmacology, food science and neurophysiology.

BACKGROUND OF THE INVENTION

New chemical substances for medicines or food additives are synthesized. Strong electromagnetic fields and magnetic fields are getting close to ourselves as we come to use electrical appliances such as personal computers or portable phones. To study effects of those new factors on us, statistical studies of human beings, and experiments using animals were conducted in associated with synthesized chemical substances, electromagnetic fields or magnetic fields.

However, results from the statistical studies of human beings were apt to be less reliable because desired experimental conditions were difficult to set. With conventional methods for studying the operation of chemical reagents on animals, the chemical reagents were injected into living individuals or administered orally. Consequently, one experiment needed at least one individual of animals. The experiments using animals were very costly, because the experiments needed a number of individuals to obtain reliable results, experimenters needed large equipments for keeping those individuals and had to carefully take care of them. Therefore, the reduction in number of animals to experiment was favorable.

It is desirable that experimenters can take extract tissues or cells from animals and keep the tissues or cells in appropriate conditions and observe the change in activities of the tissues or cells over time with the conditions changed. Methods or apparatus to keep tissues or cells in appropriate conditions, to change the conditions freely, and to permit observation of the change in activities of the tissues or cells over time have been desired to conduct experiments efficiently and at a low cost.

SUMMARY OF THE INVENTION

To solve the problem, the invention aims to provide a method which keeps tissues or cells in appropriate conditions, changes the conditions freely, and permits observation of the change in activities of the tissues or cells over time, and an apparatus for use in such method.

To obtain the aim, the invention provides a method of observing a physical and chemical property of a tissue or cell by using an apparatus which comprises at least a cell culturing means, an environment conditioning means, an observing means and a comparing means, and the method comprises steps of (A) culturing the tissue or cell by the cell culturing means, (B) maintaining a first physical and chemical environment around the tissue or cell by the cell culturing means, (C) observing a first physical and chemical property of the tissue or cell in the first physical and chemical environment by the observing means, (D) changing the first physical and chemical environment to a second physical and chemical environment by the environment conditioning means, (E) observing a second physical and chemical property of the tissue or cell in the second physical and chemical environment by the observing means, and (F) comparing the first physical and chemical property of the tissue or cell with the second physical and chemical property of the tissue or cell by the comparing means.

It is preferable in the method of the invention that the step of changing the first physical and chemical environment to the second physical and chemical environment comprises substituting a second culture medium for use in the cell culturing means for a first culture medium used in the cell culturing means.

Further, the invention provides an apparatus for measuring a physical and chemical property of a tissue or cell, and the apparatus comprises (A) means for culturing the tissue or cell and for maintaining a physical and chemical environment around the tissue or cell, (B) means for conditioning a physical and chemical environment in which the tissue or cell is maintained, (C) means for observing a physical and chemical property of the tissue or cell, and (D) means for comparing a first physical and chemical property of the tissue or cell with a second physical and chemical property of the tissue or cell. Examples of the environment conditioning means include an incubator, thermostat, pH buffer solution, electromagnetic shield, magnetic shield, camera, optic filter and a chamber in which the humidity is kept constant.

It is preferable in the apparatus of the invention that the environment conditioning means comprises means for adding a substance to a culture medium used in the cell culturing means and means for substituting a second culture medium for use in the cell culturing means for a first culture medium used in the cell culturing means.

It is preferable in the apparatus of the invention that the observing means is a potential measurement apparatus for measurement of electric physiological characteristics of a tissue or cell, and the potential measurement apparatus comprises (A) an integrated cell holding instrument provided with a plurality of microelectrodes on a substrate, a cell holding part for placing the tissue or cell thereon, and an electric connection means for providing an electric signal to the microelectrodes and for leading out an electric signal from the microelectrodes, (B) means to be connected to the electric connection means of the integrated cell holding instrument and to provide electric stimulation to the tissue or cell, and (C) means to be connected to the electric connection means of the integrated cell holding instrument and to process an output signal arising from electric physiological activities of the tissue or cell.

DETAILED DESCRIPTION OF THE INVENTION

The use of the apparatus are outlined as follows. Tissues or cells extracted from an animal are preserved in a first condition by a cell culturing means. Physical and chemical properties of the tissues or cell are examined in the first condition by an observing means. The whole or part of the first condition is changed to a second condition by an environment conditioning means. The environmental condition is changed by, for example, addition of reagents to a culture medium, or application of electromagnetic field to the tissues or cells. Afterwards, the same physical and chemical properties of the tissues or cell are examined in the second condition by the observing means. Finally, the physical and chemical properties observed in the second condition are compared with those observed in the first condition by a comparing means. Effects of the change in environment condition on the physical and chemical properties of the tissues or cells are thus examined by the above processes.

When the environment conditioning means comprises means for adding a chemical substance to a culture medium used in the cell culturing means and means for substituting a culture medium for used culture medium, environment conditions are readily changed, and experiments are conducted efficiently and subsequently. Examples of the chemical substances include narcotics and stimulant drugs.

When the observing means is the above-noted apparatus for measurement of electric physiological characteristics, an example of the use of the apparatus is as follows. Sample tissues or cells are placed on a cell holding part of an integrated cell holding instrument. A plurality of microelectrodes contact with the tissues or cells. A stimulation signal is applied to a pair of electrodes from among the microelectrodes by a stimulation signal supplying means through an electric connection means. The variation in evoked potentials generated at each of the other electrodes are conveyed to the signal processing means through the electric connection means over time. The variation in the evoked potentials are appropriately processed, and it is displayed on a screen of an image display device and stored in an image memory device. After the change of the condition in which the tissues or cells were preserved, the same measurement is conducted so that obtained new results are compared with the previous results stored in the memory device. Spontaneous active potentials generated without a stimulus signal are similarly measured.

The invention will now be described in detail by referring to the attached figures and the following examples. The examples are illustrative and should not be construed as limiting the invention in any way.

Figure 1:
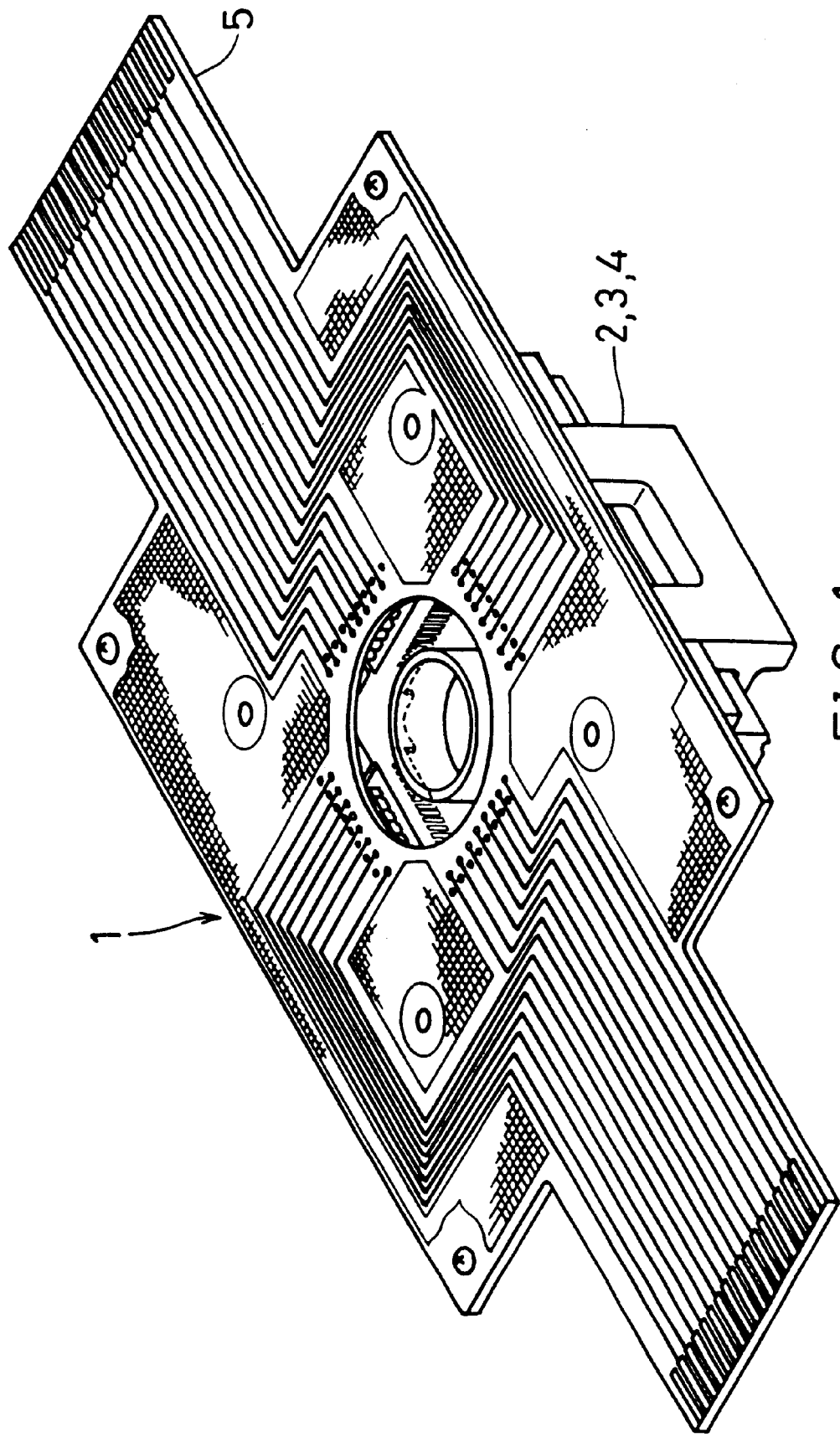
FIG. 1 is a perspective view showing an integrated cell holding instrument used for the apparatus in one embodiment of the invention.
Figure 2:
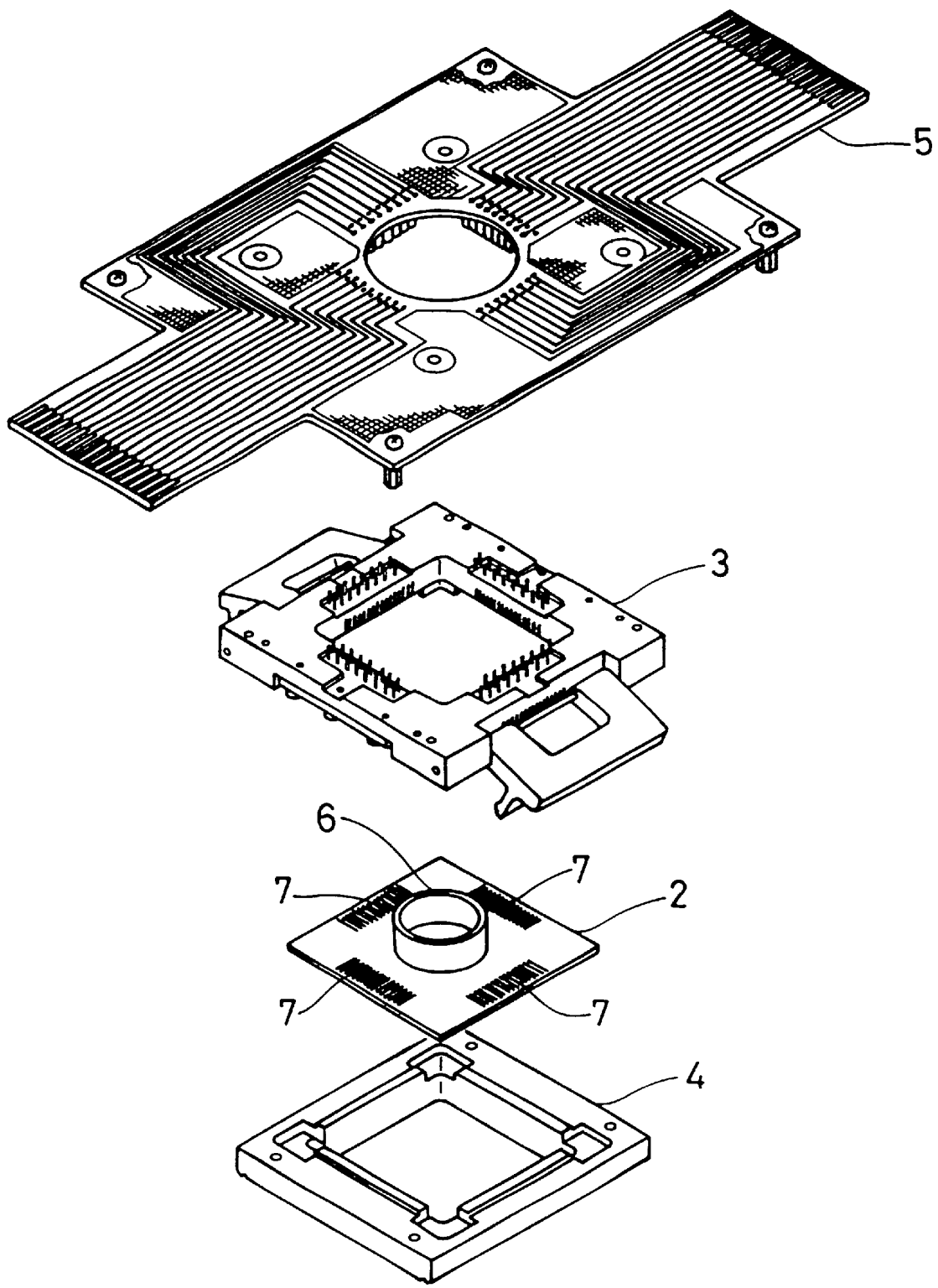
FIG. 2 is an assembly diagram of an integrated cell holding instrument.

An integrated cell holding instrument used for an apparatus of the embodiment has almost the same structure as that disclosed in JP Laid-open patent application (Tokkai Hei) No. 7-144768 and others. The integrated cell holding instrument 1, as shown as a perspective view in FIG. 1 and as an assembly diagram in FIG. 2, comprises planar electrode 2, which is disposed with a plurality of microelectrodes and their patterns on the surface of a glass plate, half-split holders 3 and 4 for fixing the planar electrode 2 by holding it from the top and bottom, and printed circuit board 5 on which these holders are fixed.

Figure 3:
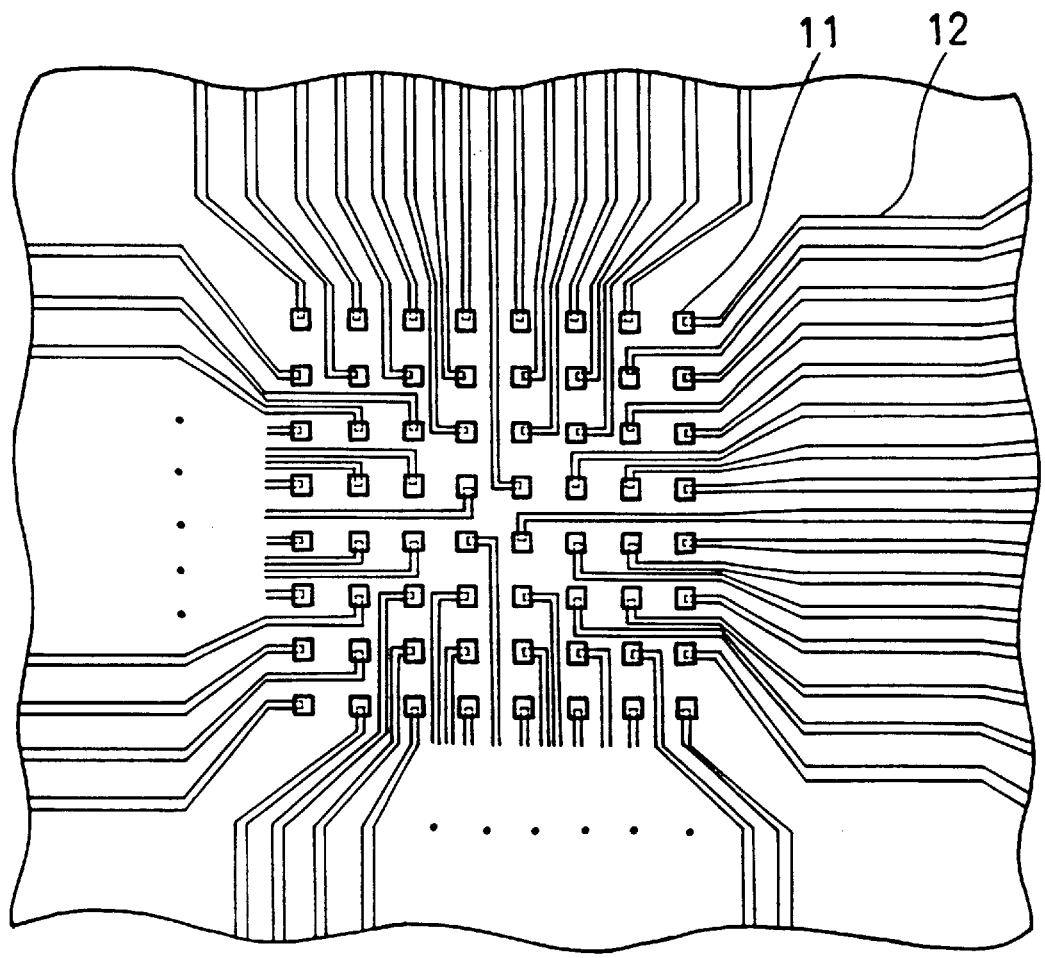
FIG. 3 is a flat diagram showing 64 microelectrodes and patterns disposed in the center of a planar electrode comprising an integrated cell holding instrument.

The planar electrode 2 is approximately the same as that disclosed in JP Laid-open patent application (Tokkai Hei) No. 6-78889 and others. The planar electrode 2 comprises a substrate made of a transparent pilex glass having a thickness of 1.1 mm and a size of 50×50 mm, and in the center of this substrate, 64 pieces of microelectrodes 11 are formed in a matrix form of 8×8, and each microelectrode is connected to conductive pattern 12 (cf. FIG. 3). Each of the electrodes 11 has a size of 50×50 $\mu$m square (area $25 \times 10^2$ $\mu m^2$), and the center-to-center distance between the adjacent electrodes is 150 $\mu$m. Furthermore, each side of the substrate has 16 pieces of electric contact points 7 formed, totalling to 64 pieces (cf. FIG. 2). These electric contact points 7 are connected with 64 pieces of the microelectrodes 11 disposed in the center of the substrate to correspond by 1 to 1 by the conductive patterns 12. Sixteen pieces of the electric contact points 7 are arranged on each side with a pitch of 1.27 mm. Cylindrical glass frame 6 (cf. FIG. 2) with an inner diameter of 22 mm, an outer diameter of 25 mm, and a height of 10 mm is adhered on the glass plate 13 using a silicone adhesive. This cylindrical frame 6 is fixed with its center matching the center of the glass plate 13, that is, the central part of 64 microelectrodes, and the inside of the frame 6 becomes a cell holding part.

Figure 4:
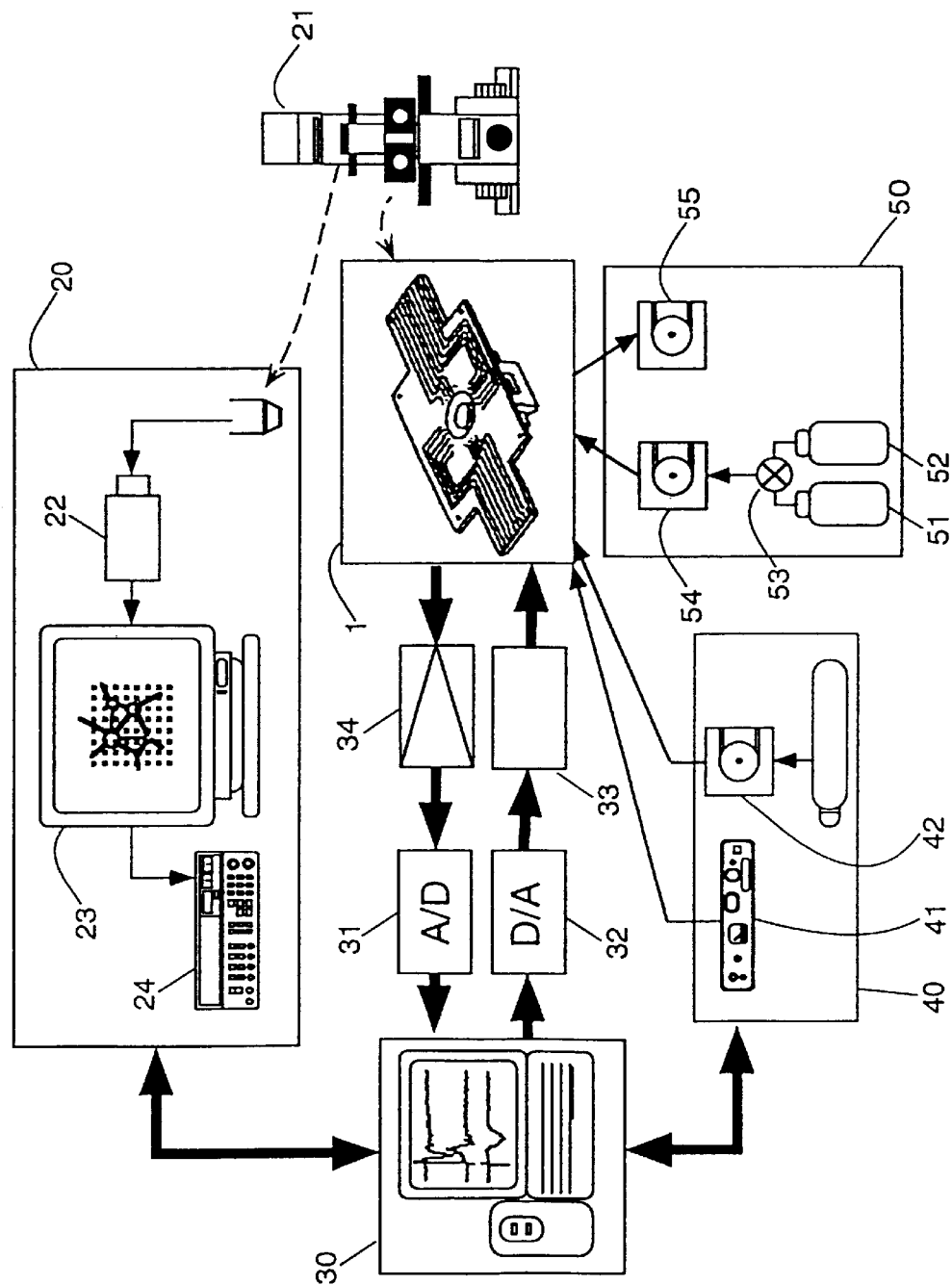
FIG. 4 is a block diagram of the apparatus in one embodiment of the invention.

A preferable configuration of the apparatus using the above-configured integrated cell holding instrument 1 is shown in FIG. 4. The apparatus of this embodiment comprises the above-mentioned integrated cell holding instrument 1, optical observation means 20 including an inverted microscope 21 for optical observations of cells which are placed in this integrated cell holding instrument 1, computer 30 including means of providing a stimulation signal to the cells and means of processing an output signal from the cells, cell culturing means 40 for culturing cells and maintaining a suitable culture medium for the cells, and chemical environment conditioning means 50 for adding an intended amount of a chemical substance to a culture medium and substituting culture media. Computer 30 is an example of means for comparing a first physical and chemical property of the tissue or cell with a second physical and chemical property of the tissue or cell. Chemical environment conditioning means 50 is an example of means for conditioning an environment in which the tissue or cell is maintained. When effects of electromagnetic fields or magnetic fields on cells are examined, chemical environment controlling means 50 is replaced with a device for generating electromagnetic fields or magnetic fields, such as a cathod-ray tube. Such device can be placed in the vicinity of the integrated cell holding instrument 1. Electrochemical properties of cells are observed while the device is not operating, and while the device is operating. The electrochemical properties of the cells which are applied with an electromagnetic field or magnetic field, or are free of such application are compared to examine effects of electromagnetic fields or magnetic fields on the cells.

Besides the inverted microscope 21 (for example, "IMT-2-F" or "IX70" manufactured by OLYMPUS OPTICAL CO., LTD.) where the integrated cell holding instrument 1 is installed, the optical observation means 20 also includes SIT camera 22 used for a microscope (for example, "C2400-08" manufactured by HAMAMATSU PHOTONICS K.K.), high-accurate display 23, and image filing device 24 (for example, "TQ-2600" or "FTQ-3100" manufactured by MATSUSHITA ELECTRIC INDUSTRIAL CO., LTD.). The term SIT camera is a general term used for cameras which apply a static induction transistor to an image pickup tube, and an SIT camera is a representative example of sensitive cameras. However, the high-accuracy display 23 can be used also as a display for the computer 30. The specific devices described above in parenthesis are illustrative examples, and the invention is not limited to these devices only.

As for the computer 30, a personal computer (for example, compatible with WINDOWS) is used which is mounted with an A/D conversion board and software for measurement. The A/D conversion board includes A/D converter 31 and D/A converter 32 shown in FIG. 4. The A/D converter 31 has 16 bits and 64 channels, and the D/A converter 32 has 16 bits and 8 channels.

The measuring software includes software for determining conditions needed for providing a stimulation signal or recording conditions of an obtained detection signal. With the use of this type of software, the computer 30 is not only capable of structuring the means of providing a stimulation signal to the cells and the means of processing the detection signal from the cells, but also is capable of controlling the optical observation means (the SIT camera and the image filing device) or the cell culturing means.

In the following, particularly useful specifications for the software for measurement will be explained. On a computer screen directed to parameter setting, it is possible to determine complicated stimulation conditions by drawing a stimulation waveform on the screen using a keyboard or a mouse. Furthermore, recording conditions are determined such that 64 input channels, a sampling rate of 10 kHz, and continuous recording over several hours are enabled. In addition, the electrode which provides a stimulation signal or the electrode which draws out a detection signal from the cells can be specified by pointing to a microscope image displayed on the screen with a mouse or a pen. Besides, various conditions such as temperature or pH of the cell culturing means 40 are determined by using a keyboard. Opening and shutting valves and pumps of environment conditioning means 50 is controlled by using a keyboard, and conditions such as flow rate for pumps are determined by using a keyboard.

A recording screen displays a spontaneous action potential or an evoked potential detected from the cells in real-time at a maximum of 64 channels.

When a stimulation signal is output from the above-configured computer 30, this stimulation signal is forwarded by way of the D/A converter 32 and isolator 33 (for example, "BSI-2" manufactured by BAK ELECTRONICS CO., LTD.) to the cells. In other words, the stimulation signal is applied between two points selected from 64 pieces of the microelectrodes 11 in the integrated cell holding instrument 1. Then, an evoked potential arising between each of the microelectrodes 11 and a GND level (potential of culture solution) is input to the computer 30 via 64 channels of a sensitized amplifier 34 (for example, "AB-610J" manufactured by NIHON KODEN CO., LTD.) and the A/D converter 31. The amplification factor of the amplifier 34 was 100 dB, and the frequency band was from 0 to 10 kHz. However, when an evoked potential by a stimulation signal is measured, the frequency band was determined to be from 100 Hz to 10 kHz using a low cut filter.

Next, the cell culturing means 40 is provided with temperature adjuster 41, solution circulation means 42, and means 43 for supplying a mixed gas of air and carbon dioxide. Actually, the cell culturing means 40 can comprise a product equivalent to a microincubator such as "PDMI-2", a product equivalent to a temperature controller such as "TC-202" (both products manufactured by MEDICAL SYSTEMS CO., LTD.) and a $CO_2$ gas cylinder. This microincubator can control the temperature in the range of 0 to 50° C. by a Peltier element. A liquid delivery rate can be set below 3.0 ml/min, and an air supply rate can be set below 1.0 l/min. Alternatively, a microincubator integrated with a temperature controller (for example, "IMT2-IBSV" manufactured by OLYMPUS OPTICAL CO., LTD.) can be used.

As shown in FIG. 4, environment conditioning means 50 comprises solution bottles 51 and 52, valve 53, and pumps 54 and 55. Solution bottle 51 contains a culture medium for normal culture. Solution bottle 52 contains a sample solution of the culture medium and a chemical substance. Switching valve 53 can allow either the culture medium or the sample solution to flow into cell holding part 4 by pump 54. Pump 55, which is synchronized with pump 54, absorbs a solution in cell holding part 4 at a speed which pump 54 sends a solution. It is possible to change a composition of a solution within cell holding part 4 while the amount of a solution within cell holding part 4 is kept constant.

By using the above-mentioned apparatus, nerve cells or tissues were actually cultured on the integrated cell holding instrument, culture conditions were changed, and the potential variation accompanied by activities of the nerve cells or nerve tissues were measured before and after the change.

EXAMPLE 1

An example of the measurement will be explained hereinafter. A cerebral cortex section of rats were used as the nerve organs, which were cultured according to a method which will be described later on in an embodiment. Evoked potentials generated due to stimulation signals were measured before and after the addition of a stimulant drug, methamphetamine, to the culture medium.

Figure 5A:
FIGS. 5(a) through 5(e) are waveforms of the evoked potential recorded in one embodiment of the invention.
Figure 5B:
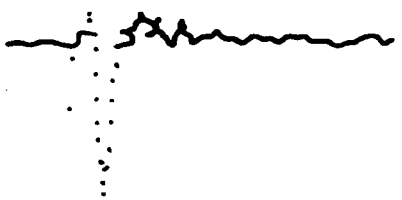
Figure 5C:
Figure 5D:
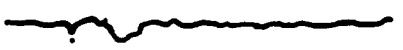
Figure 5E:
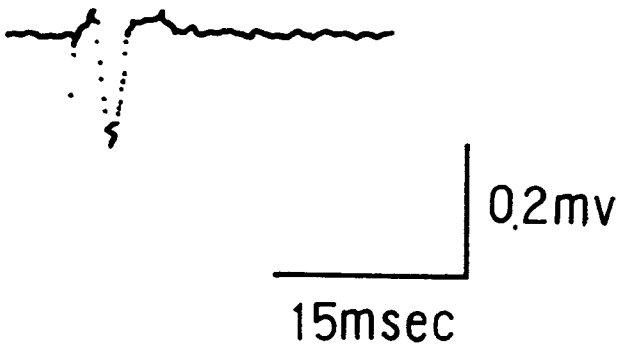
Figure 6A:
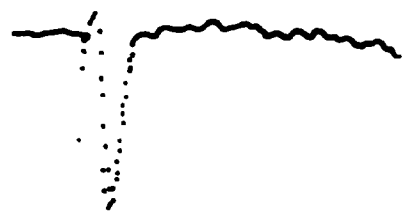
FIGS. 6(a) through 6(c) are waveforms of the evoked potential recorded in one embodiment of the invention.
Figure 6B:
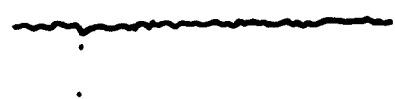
Figure 6C:
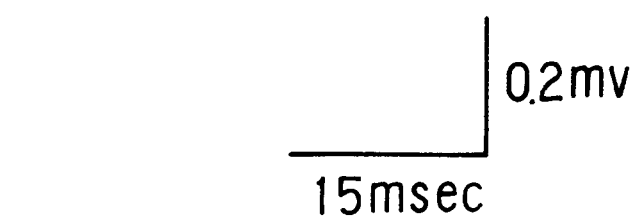

Prior to culture of the cells, the surface of a planar electrode was covered with collagen gel for the purpose of enhancing the adhesive property of each electrode in the planar electrode with the cells. In other words, collagen gel with a thickness of 50 $\mu$m or less was formed on the surface of each electrode coated with platinum black and also on the surface of an insulation coating in the vicinity thereof as mentioned above. Then, on top of the collagen gel, and also where a microelectrode is present, a section of cerebral cortex of rats (thickness of 500 $\mu$m or less) was placed and cultured. FIGS. 5(b) through 5(e) show waveforms of the evoked potential before or after 30 min of the addition of methamphetamine (0.1 mM, 0.5 mM, or 1.0 mM) to the culture medium in the sixth day of the culture. FIG. 5(a) shows a waveform of the evoked potential measured in a control experiment using a culture medium containing no methamphetamine. FIG. 6(b) through 6(c) show waveforms of the evoked potential before or after 3 days of the addition of methamphetamine (0.01 mM or 0.1 mM) to the culture medium in the third day of the culture. FIG. 6(a) shows a waveform of the evoked potential measured in a control experiment using a culture medium containing no methamphetamine. In other words, FIGS. 5 show acute effects of methamphetamine, and FIGS. 6 show chronic effects of methamphetamine.

FIG. 5(a) shows the evoked potential measured using a normal medium containing no methamphetamine. FIG. 5(b) shows that 0.1 mM of methamphetamine had no acute effect on the evoked potential. FIG. 5(c) shows that 0.5 mM of methamphetamine made the amplitude of the waveform small. FIG. 5(d) shows that 1 mM of methamphetamine abolished the evoked potential. FIG. 5(e) shows that the evoked potential which was measured 30 minutes after the medium was substituted from the medium containing 1 mM methamphetamine to the normal medium containing no methamphetamine. The substitution reproduced the original waveform of the evoked potential, as shown in FIG. 5(a). It seems that the acute application of methamphetamine produces reversible changes in the evoked potential.

FIG. 6(a) shows the evoked potential measured using a normal medium containing no methamphetamine. FIG. 6(b) shows that 0.01 mM of methamphetamine abolished the evoked potential. FIG. 6(c) shows that 0.1 mM of methamphetamine also abolished the evoked potential completely. The evoked potential was still suppressed 30 minutes after the medium was substituted from the medium containing 0.1 mM methamphetamine to the normal medium containing no methamphetamine. It seems that the chronic administration, i.e., for 3 days, of methamphetamine produces irreversible changes in the evoked potentials.

Next, examples of a suitable culture method for cerebral cortex slices will be explained.

1) Culture Medium

The following additives were added to a culture medium in which Dulbecco modified Eagle's medium and HamF-12 medium were mixed in a volume ratio of 1:1 (media manufactured by GIBCO CO., LTD. 430-2500EB).

glucose, GIBCO CO., LTD. 820-5023IN, 2.85 mg/L (totalling to 6 mg/L together with glucose contained originally in the above-mentioned culture medium)

putrescine, SIGMA CO., LTD. P5780, 100 μM progesterone, SIGMA CO., LTD. P8783, 20 nM hydrocortisone, SIGMA CO., LTD. H0888, 20 nM sodium selenite, WAKO CO., LTD. 198-0319, 20 nM insulin, SIGMA CO., LTD. I6634, 5 mg/L transferrin, SIGMA CO., LTD. T147, 100 mg/L sodium bicarbonate, CO., LTD. 2.438 g/L addition of a suitable amount of 1N HCl or 1N NaOH to adjust to pH 7.4

After the above-mentioned additives were added, filtration and sterilization were conducted, and the culture medium was preserved at 4° C. and ready to be used. This culture medium is hereinafter simply called "culture medium".

2) Structure of a Well on a Planar Electrode

For the convenience of culturing nerve cells or nerve organs on a planar electrode, a polystyrene cylinder having an inner diameter 22 mm, an outer diameter 26 mm, and a height 8 mm was adhered in the following steps.

(a) On the bottom face of a polystyrene cylinder (inner diameter 22 mm, outer diameter 26 mm, height 8 mm), a sufficient amount of a one-liquid silicon adhesive (DOW CORNING CO., LTD. 891 or SHIN-ETSU CHEMICAL CO., LTD. KE-42RTV) was applied.

(b) The center of a glass substrate in the planar electrode and the center of the polystyrene cylinder were carefully matched and then adhered in this state.

(c) By leaving it in an environment in which dust hardly enters for 24 hours, the adhesive was solidified.

(d) After dipping in 70% ethanol for 5 minutes, sterilization was conducted by air-drying inside a clean bench, which is then ready for processing the electrode surface.

3) Processing of the Electrode Surface

In order to enhance cell adhesive property on the surface of a planar electrode, collagen gel was formed on the surface of the electrode by the following method. All of these operations were conducted under a sterilized atmosphere.

(a) Solutions A, B, and C were prepared and iced.

A. Diluted hydrochloric acid collagen solution, 0.3 vol. % (pH 3.0, NITTA GELATIN CO., LTD. Cellmatrix Type I-A)

B. Solution comprising a mixture medium of Dulbecco modified Eagle's medium and HamF-12 medium mixed in a volume ratio of 1:1 (GIBCO CO., LTD. 430-2500EB), which is not provided with sodium bicarbonate and is made with a concentration 10 times higher than for an ordinary use, and then filtration and sterilization were conducted thereto.

C. Sodium bicarbonate (2.2 g) and HEPES (4.77 g, manufactured by GIBCO CO., LTD. 845-1344 IM) were dissolved in 100 mL of 0.05 N sodium hydroxide solution, and filtration and sterilization were conducted thereto.

(b) While cooling, the solutions A, B, and C were mixed at a volume ratio of 8:1:1. At this time, A and B are first mixed thoroughly and C is added afterwards to be mixed.

(c) In a well of a planar electrode which was cooled in advance to about 4° C. , 1 mL of the mixed solution of (b) was injected little by little. After the entire electrode surface was covered, the mixed solution was removed as much as possible with a glass Pasteur pipette. Through this operation, a coating of the mixed solution was formed on the electrode surface with a thickness of 50 μm or less.

(d) By heating the planar electrode disposed with the mixed solution coating at 37° C. for 30 minutes, gelatinization of the mixed solution took place, and a collagen gel matrix was formed.

(e) 1 mL of sterilized water was added into the well of the planar electrode, and about 5 minutes thereafter, the water was removed, thereby washing.

(f) The operation of Step (e) was repeated two more times (a total of 3 times).

(g) The culture medium 1 mL (excluding insulin and transferrin) was injected little by little into the well of the planar electrode, and preserved inside a $CO_2$ incubator under the conditions of temperature 37° C., relative humidity 97% and higher, $CO_2$ concentration 5%, and air concentration 95%, which is then ready for use.

4) Culture of Nerve Cells or Nerve Organs

Generally, culture forms can be divided into two types. That is, a dissociated cell culture of nerve cells and an organotypic slice culture of a nerve organ. Each form will be explained in the following.

4-1) Dissociated Culture of Cerebral Visual Cortex Nerve Cells of Rats

The following operations were all performed in a sterilized atmosphere.

(a) Brains of fetuses of SD rats at 16–18 days of pregnancy were removed and immersed in iced Hanks' Balanced Salt Solution (manufactured by GIBCO CO., LTD. 450-1250EB).

(b) From the brains in the iced Hanks' Balanced Salt Solution, visual cortices were cut out and transferred to minimum essential medium liquid (manufactured by GIBCO CO., LTD. 410-1100EB).

(c) In the minimum essential medium liquid, the visual cortices were cut into as small pieces as possible, 0.2 mm square at maximum.

(d) The visual cortices cut into small pieces were placed in test tubes for centrifugal separation, and after washing with Hanks' Balanced Salt Solution free from calcium and magnesium three times, they were dispersed in a suitable volume of the same liquid.

(e) In the test tubes for centrifugal separation of Step (d), Hanks' Balanced Salt Solution free from calcium and magnesium with trypsin dissolved at 0.25% was added to double the total volume. With gentle stirring, enzymatic processes were allowed to take place while the solution was constantly kept at 37° C. for 15 minutes.

(f) To the culture medium shown in 1) (containing additives), 10 vol. % of fetal cow serum was added, which is then placed in the test tubes for centrifugal separation subjected to Step (e) to further double the total volume. With a glass Pasteur pipette having a reduced diameter produced by fire-polishing the tip end with a burner, gently repeating pipetting (about 20 times at maximum), the cells were unravelled.

(g) Centrifugation was carried out for 5 minutes at 9806.65 m/sec$^2$ (that is, 1000 g). Upon completion of centrifugation, the supernatant was discarded and the precipitate was suspended in the culture medium containing 5 vol. % of fetal cow serum.

(h) Step (g) was repeated two more times (a total of 3 times).

(i) The precipitate finally obtained was suspended in the culture medium containing 5 vol. % fetal cow serum, and using an erythrocytometer, the cell concentration in the suspension liquid was measured. After the measurement, using the similar culture medium, the cell concentration was adjusted to be $2 \times 10^6$ to $4 \times 10^6$ cells/ml.

(j) A planar electrode which was preserved in a $CO_2$ incubator after subjected to the process of above steps 1–3) was taken out, and the culture medium (free from insulin and transferrin) inside a well is removed, and 500 µL of a culture medium containing 5% of fetal cow serum was newly injected little by little. Furthermore, 100 µL of the cell suspension liquid with the cell concentration adjusted according to Step (i) was gently added and again let stand in the $CO_2$ incubator.

(k) Three days after the performance of Step (j), one half the culture medium was replaced with a new one. For the replaced medium, the culture medium not containing fetal cow serum was used. By reducing the concentration of fetal cow serum, growth of cells other than nerve cells (for example, glial cells) can be suppressed.

(l) Thereafter, half of the medium was replaced in a similar manner every 1 to 2 days.

4-2) Culture Method of a Cerebral Cortex Section of Rats (a) Brains of SD rats 2 days old were removed and immersed in iced Hanks' Balanced Salt Solution containing 0.25 vol. % of D-glucose.

(b) In the iced Hanks' Balanced Salt Solution containing 0.25 vol. % of D-glucose, cerebral meninges attached on the brain are removed using a sharp-edged pincette very carefully not to damage the cerebral cortex.

(c) About 500 µm away from a callous body, a hemisphere of the cerebral cortex without the cerebral meninges was cut from the occipital lobe side to the frontal lobe side along the callous body by means of microscissors used for surgical operations of eyes.

(d) Subsequently, using the microscissors used for surgical operations of eyes, a cerebral cortex was cut out vertically to the cross-section of Step (c) with a thickness of 200 to 300 µm to create a section.

(e) The microscissors used for surgical operations of eyes are used further to adjust a size of the section to be about 1×1 mm.

(f) The planar electrode prepared in the above-mentioned "3) Processing of an electrode surface" was taken out from the $CO_2$ incubator, and the cerebral cortex section whose size was adjusted was sucked up with a pipette having a diameter of 2 mm and larger very gently not to damage the section, and then transferred into a culture well of the planar electrode.

(g) With a Pasteur pipette with the tip end fire-polished with a burner, the material was arranged on the electrode such that the layer structure of the cortex faces upward and is placed on the electrode, while being careful not to damage the cerebral cortex section.

(h) After the cerebral cortex section is placed on the planar electrode, the amount of the culture medium was adjusted so that a base of the section touched the culture medium and the top face was exposed to outside air.

(i) After adjusting the culture medium amount, the planar electrode was placed in a sterilized Petri dish, and about 5 ml of sterilized water at 37° C. was injected little by little into the Petri dish to prevent the culture medium from drying, and again let stand in the $CO_2$ incubator.

(j) Thereafter, the medium was replaced with a new one once every day while attending to the amount of culture medium. The culture medium amount was determined to be the same as in Step (h).

EXAMPLE 2

For an example of non-nerve tissues, a heart section of rats were used as a non-nerve tissues, which were cultured according to a method which will be described later on in an embodiment. The variation in spontaneous action potentials were recorded in the following two conditions (i) before and after the addition of acetylcholine (Ach) to the culture medium, or (ii) before and after the addition of adrenaline to the culture medium. The culture medium used was the same as in Example 1. The structure used of a well on a planar electrode and the processing of the electrode surface were the same as in Example 1. Prior to culture of the cells, the surface of a planar electrode was covered with collagen gel (thickness of 50 µm or less) for the purpose of enhancing the adhesive property of each electrode in the planar electrode with the cells. Then, on top of the collagen gel, and also where a microelectrode is present, a section of heart of rats was placed and cultured. The section of heart of rats was prepared to include sinoatrial node or atrioventricular node.

Figure 7A:
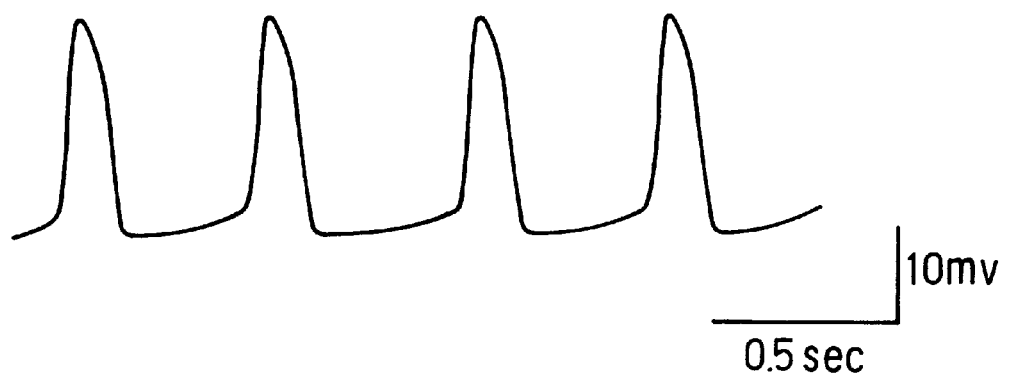
FIGS. 7(a) and 7(b) are waveforms of the spontaneous active potential recorded in one embodiment of the invention.
Figure 7B:
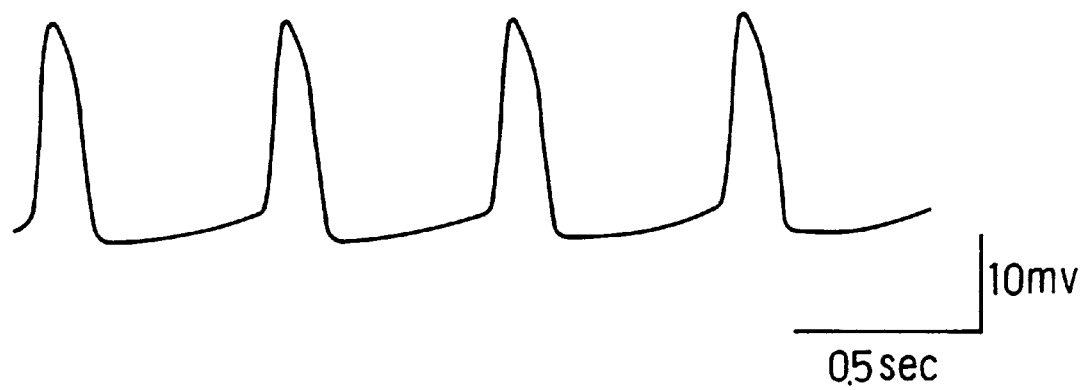

FIGS. 7(a) and 7(b) show spontaneous active potentials of the cells in the fifth day after the culture before and the addition of Ach to the culture medium. Ach is a chemical transmitter to be secreted from a terminus of parasympathetic nerves upon stimulation. Ach usually works to reduce the blood pressure and heartbeats, to contract the intestine tube and skeletal muscles. As shown in FIG. 7(B), a spontaneous active potential was apparently reduced after the addition of acetylcholine to a final concentration of 1 mM, compared with before the addition (cf. FIG. 7(a)).

Figure 8A:
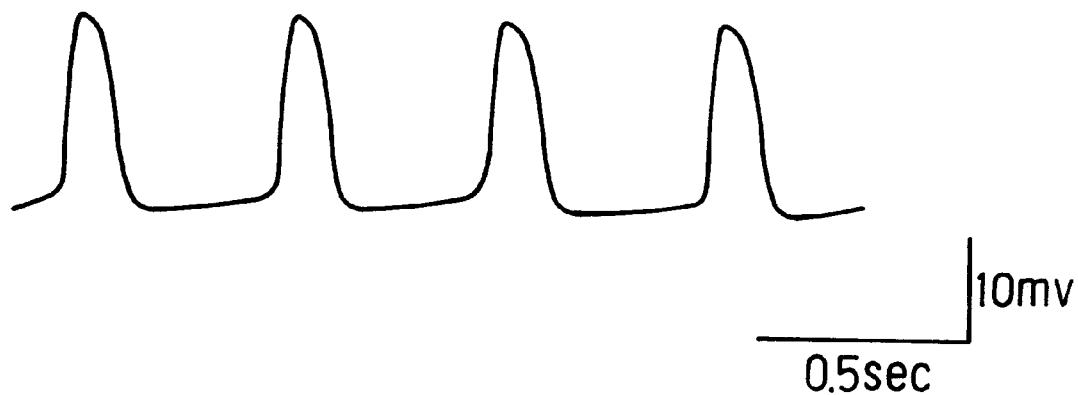
FIGS. 8(a) and 8(b) are waveforms of the spontaneous active potential recorded in one embodiment of the invention.
Figure 8B:
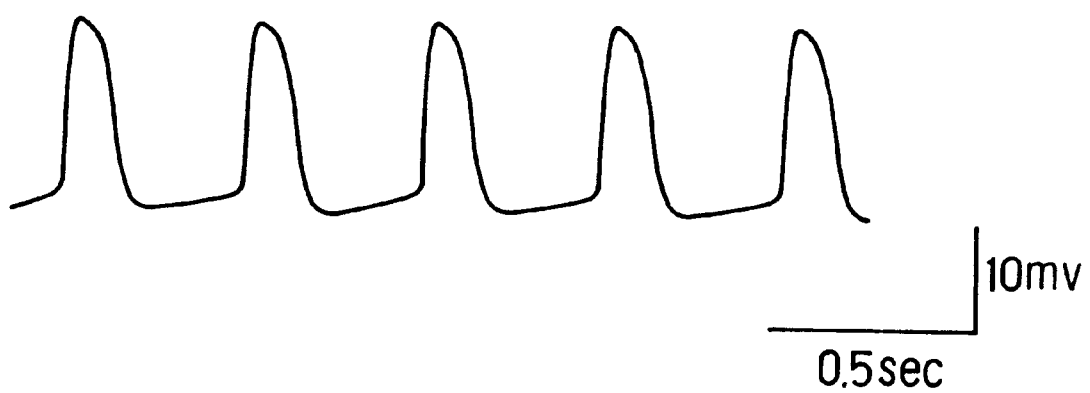

FIGS. 8(a) and 8(b) show spontaneous active potentials of the cells in the fifth day after the culture before and after the addition of adrenaline to the culture medium. Adrenaline is known to enhance the contraction of a heart muscle. As shown in FIG. 8(B), a spontaneous active potential was apparently raised after the addition of adrenaline at a final concentration of 1 mM, compared with before the addition (cf. FIG. 8(a)).

Next, examples of a suitable culture method for heart slices will be explained.

1) Culture Medium

The same culture medium as in Example 1 was used.

2) Structure of a Well on a Planar Electrode

Wells were prepared in the same manner as in Example 1.

3) Processing of the Electrode Surface

The electrode surface was processed in the same manner as in Example 1.

4) Culture of Heart Sections

The heart sections were cultured in the similar manner to that of a cerebral cortex section of rats (Section 4-2). Details of the culture are as follows.

(a) Hearts of SD rats 2 days old were removed and immersed in iced Hanks' Balanced Salt Solution containing 0.25 vol. % of D-glucose. Hanks' Balanced Salt Solution was exchanged several times to remove blood from the hearts.

(b) The hearts were carefully cut open to prepare sections including sinoatrial node or atrioventricular node.

(c) The sections were cut to have a size of 1×1 mm with microscissors used for surgical operations of eyes.

(d) The planar electrode prepared in the above-mentioned "3) Processing of an electrode surface" was taken out from the $CO_2$ incubator, and the heart section whose size was adjusted was sucked up with a pipette having a diameter of 2 mm and larger very gently not to damage the section, and then transferred into a culture well of the planar electrode.

(e) With a Pasteur pipette with the tip end fire-polished with a burner, the section was arranged on the electrode, while being careful not to damage the heart section.

(f) After the heart section is placed on the planar electrode, the amount of the culture medium was adjusted so that a base of the section touched the culture medium and the top face was exposed to outside air.

(g) After adjusting the culture medium amount, the planar electrode was placed in a sterilized Petri dish, and about 5 ml of sterilized water at 37° C. was injected little by little into the Petri dish to prevent the culture medium from drying, and again let stand in the $CO_2$ incubator.

(h) Thereafter, the medium was replaced with a new one once every day while attending to the amount of culture medium. The culture medium amount was determined to be the same as in Step (f).

In the above examples, methamphetamine, acetylcholine or adrenaline was contained in a sample solution. Instead, other chemical substance such as medicines can be contained in a sample solution to examine the operation of the substances.

As explained above, the embodiment provides a method or apparatus for keeping tissues or cells in appropriate conditions, changing the conditions freely, and permitting observation of the change in activities of the tissues or cells over time. The method and the apparatus are be suitable for studying effects of chemical substances which did not exist in the nature world, strong electromagnetic field or magnetic field on biological tissues. When effects of, for example, a magnetic field on biological tissues are examined, the apparatus can be disposed with a device for generating a magnetic field inside of a shield.

The method of the invention can be directed to experiments to obtain as many data as possible from one individual, because many samples are taken from one individual. Consequently, the use of the apparatus is helpful for reducing the number of animals used in experiments.

The invention may be embodied in other forms without departing from the spirit or essential characteristics thereof. The embodiments disclosed in this application are to be considered in all respects as illustrative and not as restrictive. The scope of the invention is indicated by the appended claims rather than by the foregoing description, and all changes which come within the meaning and range of equivalency of the claims are intended to be embraced therein.

What is claimed is:

1. A method for observing electrical waveforms in a tissue slice by providing an apparatus which comprises at least cell culturing components, environment conditioning components for changing a culture medium or the physical or chemical property of the tissue slice, a plurality of electrodes on a substrate, said electrodes being of a sufficient number to allow detection and stimulation of electrical waveforms in said tissue slice, and a comparator, the method comprising the steps of:

(A) culturing the tissue slice by the cell culturing components;

(B) maintaining a first physical and chemical environment around the tissue slice by the cell culturing components;

(C) observing a first complete electrical waveform of the tissue slice in the first physical and chemical environment by the plurality of electrodes;

(D) changing the first physical and chemical environment to a second physical and chemical environment by the environment conditioning components;

(E) observing a second complete electrical waveform of the tissue slice in the second physical and chemical environment by the plurality of electrodes; and (F) comparing the first electrical waveform of the tissue slice with the second electrical waveform of the tissue slice by the comparator.

2. The method of claim 1 wherein the step of changing the first physical and chemical environment to a second physical and chemical environment comprises substituting a second culture medium for use in the cell culturing components for a first culture medium used in the cell culturing components.

3. A method for observing electrical waveforms in a tissue slice by using an apparatus which comprises at least cell culturing components, environment conditioning components for changing a culture medium or the physical or chemical property of the tissue slice, a plurality of electrodes on a substrate, said electrodes being of a sufficient number to allow detection and stimulation of electrical waveforms in said tissue slice, and a comparator, the method comprising the steps of:

(A) culturing the tissue slice by the cell culturing components;

(B) maintaining a first physical and chemical environment around the tissue slice by the cell culturing components;

(C) observing a first electrical waveform of the tissue slice in the first physical and chemical environment by the plurality of electrodes;

(D) electrically stimulating said tissue slice by the plurality of electrodes;

(E) observing a second electrical waveform of the tissue slice in the second physical and chemical environment by the plurality of electrodes; and (F) comparing the first electrical waveform of the tissue slice with the second electrical waveform of the tissue slice by the comparator.

4. The method of claim 3 further including a step of changing the first physical and chemical environment to a second physical and chemical environment by substituting a second culture medium for a first culture medium used in the cell culturing components.

5. The method of claim 1 further comprising the step of stimulating said tissue slice after said step (B).

6. The method of claim 1 further comprising the step of stimulating said tissue slice after said step (D).

7. The method of claim 1 wherein the tissue slice is a neural or muscle tissue.

8. The method of claim 1 wherein the tissue slice is postnatal.

9. The method of claim 1 wherein the detection and stimulation of electrical waveforms is performed by the electrodes on the substrate.

10. The method of claim 1 further comprising repeating steps (E) and (F) until a chronic effect is observed in said second electrical waveform.

11. The method of claim 1 wherein step (E) is conducted at least three days after step (D).

12. The method of claim 1 wherein said electrodes each having an electrode area of $4\times10^2$ $\mu m^2$ to $4\times10^4$ $\mu m^2$.

13. The method of claim 3 wherein each of said electrodes is coated with a covering for increasing the adhesion of the tissue slice to said plurality of electrodes.

14. The method of claim 13 wherein said covering comprises collagen.

15. The method of claim 14 wherein said collagen has a thickness of about 50 $\mu m$ or less.

* * * * *